US008033980B2

(12) United States Patent
Van't Hooft

(10) Patent No.: US 8,033,980 B2
(45) Date of Patent: Oct. 11, 2011

(54) METHOD FOR LOCATING A SOURCE IN A BODY

(75) Inventor: Eric Van't Hooft, Brasschaat (BE)

(73) Assignee: Isodose Control Intellectual Property B.V., Veenendaal (NL)

( * ) Notice: Subject to any disclaimer, the term of this patent is extended or adjusted under 35 U.S.C. 154(b) by 0 days.

(21) Appl. No.: 11/744,515

(22) Filed: May 4, 2007

(65) Prior Publication Data

US 2007/0270626 A1    Nov. 22, 2007

(30) Foreign Application Priority Data

May 4, 2006  (NL) ..................................... 1031751

(51) Int. Cl.
*A61N 5/00*  (2006.01)
(52) U.S. Cl. ........................................................... 600/7
(58) Field of Classification Search .................. 600/1–8; 606/3
See application file for complete search history.

(56) References Cited

U.S. PATENT DOCUMENTS

| | | | | |
|---|---|---|---|---|
| 5,084,001 A | * | 1/1992 | Van't Hooft et al. | ............. 600/3 |
| 5,092,834 A | | 3/1992 | Bradshaw et al. | |
| 6,061,588 A | | 5/2000 | Thornton et al. | |
| 6,540,655 B1 | * | 4/2003 | Chin et al. | ......................... 600/3 |
| 6,582,417 B1 | | 6/2003 | Ledesma et al. | |

FOREIGN PATENT DOCUMENTS

| | | |
|---|---|---|
| DE | 36 43 902 A1 | 6/1990 |
| EP | 0 791 374 B1 | 8/1995 |
| WO | WO 99/34869 | 7/1999 |

OTHER PUBLICATIONS

International Search Report NL1031751.

* cited by examiner

*Primary Examiner* — John Lacyk
(74) *Attorney, Agent, or Firm* — Leydig, Voit & Mayer, Ltd

(57) ABSTRACT

The invention relates to a source guide apparatus for guiding and locating a radiation source in a human body, wherein a catheter is provided in a body and connected to the apparatus, and wherein the proximal end is kept in a predetermined position with respect to the body. According to the invention, a treatment window is set, which is situated within the body, within which the source can be kept in respective positions, wherein the treatment window has a fixed window width and a reference position situated at a predetermined distance with respect to the proximal end of the catheter. The source guide apparatus guides the source through the catheter to a predetermined position in the body, measured relative to the treatment window.

12 Claims, 5 Drawing Sheets

METHOD FOR LOCATING A SOURCE IN A BODY

FIELD OF THE INVENTION

The invention relates to a source guide system for guiding and locating a radiation source in a human body. The invention also relates to a method for locating a radiation source in a human body.

BACKGROUND

Such source guide systems, also called remote afterloader systems, are used with brachytherapy treatments. With such treatments, a patient is internally irradiated by means of inserted radiation sources, for the treatment of tumors. For this, one or more catheters are provided in the tissue. For this, many designs are possible, while, in addition, the position of the catheters may vary from patient to patient and the shape of the area to be irradiated may vary.

For obtaining an optimal radiation dose, various source positioning systems are used in determining the dwell positions of the source within these catheters. The length of the inserted catheter is then typically a fixed length so that always a part of the catheter needs to project outside the patient. The irradiation then takes place from the distal part of the catheter. This often has to do with the source guide system. These source guide systems often take the source out to a fixed length and then withdraw the source to the predetermined dwell positions. Other designs operate reversely; they take the source to a first position in the catheters and then step forwards to the indicated positions. The source positions and the actual position in mm need to be calculated each time. In addition, these systems typically have a maximum number of dwell positions for the source. The result of this is that, with larger irradiation areas, a plurality of these limited dwell positions results in larger step positions of for instance about 2.5 mm or about 5 mm or about 10 mm.

In order to determine these positions, often, per catheter, marker wires are provided in the catheters. On these marker wires, at every cm, markers are clamped on the wires which are then made visible by means of X-rays. Then, often a very large number of marker points arise on the X-rays which complicate determining positions and can easily be confused.

This results in a very complicated and laborious process where measuring errors regularly occur which can result in incorrect irradiations. Further, one or more catheters project far outside the patient, which can bend between irradiations or can result in movement restrictions for the patient.

SUMMARY OF THE INVENTION

In one aspect of the invention, it is an object to prevent measuring errors, save much preparation time, allow a more exact irradiation to be carried out and offer a great improvement by use of different mutual catheter lengths.

In another aspect of the invention, it is an object to allow a patient to move freely between successive treatments.

Accordingly, the invention provides the measures according to claim 1. In particular, according to the invention, a source guide system of the above-mentioned type is provided, comprising a setting unit for setting source positions and source dwell times in a treatment window, which expands from a reference position to positions situated within the body, and where the reference position is situated on or near the proximal end of the catheter; and a control unit for guiding the source through the catheter to a predetermined position in the body, according to source positions indicated by the setting unit, measured relative to the treatment window. Thus, the source positions can be determined with respect to a reference position which is situated on or near the proximal end of the catheter.

According to another aspect, the invention provides the measures according to claim 11. In particular, according to the invention, a method is provided for locating a radiation source in a human body, which source is provided in a catheter and is connected to a source guide apparatus, and where the proximal end of the catheter is situated in a predetermined position with respect to the body, comprising: defining a treatment window, which expands from a reference position to positions situated within the body, and where the reference position is situated on or near the proximal end of the catheter; and locating the source relative to the treatment window.

According to a further aspect, the invention provides a marker system, while, in a catheter, for one fixed m, a marking is provided at a distance of m×100 mm with respect to the reference position, m being a natural number, for representing an active range of m×100 mm.

BRIEF DESCRIPTION OF THE OF THE DRAWINGS

The invention will be explained in more detail with reference to the description of the drawings, in which.

DETAILED DESCRIPTION

Figure 1:
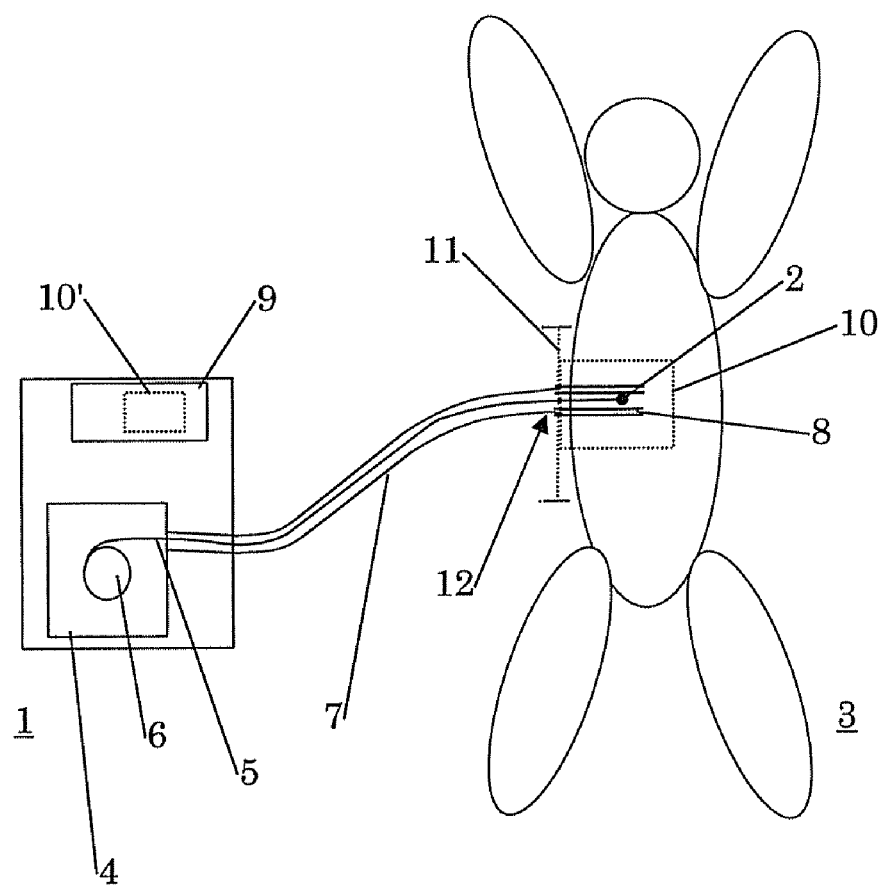
FIG. 1 shows a source guide system according to an embodiment of the invention.

FIG. 1 shows a schematic representation of an embodiment according to the invention. In the Figure, a source guide system 1 is shown for guiding and locating a radiation source 2 in a human body 3 for brachytherapy applications. Such an apparatus 1 comprises a screening housing 4, in which the radioactive source 2 is stored, if not in use. In the Figure, a condition is shown where the source 2 is taken out of the housing 4 and emits radiation in the human body 3. This, for instance, takes place by guiding the source 2 via a guide wire 5, which guides the source 2 into and out of the housing via a movement mechanism 6, via a guide tube 7. The guide tube 7 has connection to a catheter 8 inserted into the body 3, to the positions to be irradiated.

According to the invention, the apparatus 1 comprises a setting unit 9 for setting a treatment window 10. The setting unit 9 is schematically shown in FIG. 1 and may be user-interactive, for instance with a screen and a keyboard or a coupling to a computer or the like. The treatment window 10' set in the apparatus defines an actual treatment window or treatment area 10 for treating tissues in the human body 3. In this treatment window 10, predetermined positions, the so-called dwell positions, are taken up by the source 2 to achieve an optimal irradiation result for the body 3 according to a predetermined schedule. To this end, the guide apparatus 1 can keep the source 2 in a number of fixed, presettable positions in the treatment window 10, which are, for instance, always spaced about 1 mm apart, while a movement mechanism 6 comprises, for instance, a stepping motor to guide the source through in a stepwise manner.

In this manner, it is achieved that the tissues within the treatment window 10 are exposed to a desired irradiation profile. According to the invention, the treatment window 10 is chosen such that it expands from a reference position 11 to positions situated within the body 3. Within the treatment window 10, the source 2 is kept in respectively set positions. Here, the reference position 11 is chosen to be situated at a predetermined distance with respect to the proximal end 12 of the catheter 8. The apparatus further comprises a control unit (not shown) for guiding the source 2 through the catheter 8 to a predetermined position in the body 3, according to source positions indicated by the setting unit 9, measured relative to the treatment window 10.

One aspect of the invention is that the proximal end 12 of the catheter 8 is kept at a predetermined distance with respect to the body, in particular that it preferably ends directly outside the body 3. This has the advantage that a patient can be uncoupled from the apparatus and can further move freely without being hindered by projecting catheters. In one embodiment, this can be achieved by cutting off the proximal part of the catheter 8 directly outside the body, as illustrated in more detail with reference to FIG. 5.

As will be explained in more detail with reference to FIG. 2, it is preferred that fixed sizes are used of the catheters and guide tubes used, so that position determination of the source in the body is as transparent as possible. Therefore the guide tube 7, if used, preferably has a fixed distance, for instance about 1000 mm, or at least a distance of, for instance (without limitation), l×100 mm (l being a natural number). In this manner, the risk of mistakes is considerably reduced. It is also preferred that the window width has a fixed value, for all treatments to be carried out by the apparatus 1, and a catheter 8 needs to be used with an active range, measured with respect to the reference position 11, to fall within the range of this window width. A practical window width is, for instance, n×100 mm, n being a natural number, more in particular for instance about 400 mm, while the catheters, explained in more detail with reference to FIG. 2, can have an active range of, for instance, about 100, about 200 and about 300 mm, or a different active range which is within the range of the treatment window 10, by cutting off the catheter 8. The invention provides, however, that within a specific treatment episode the determination of the active range is precisely made in accordance with the programmed instructions provided.

Figure 2:
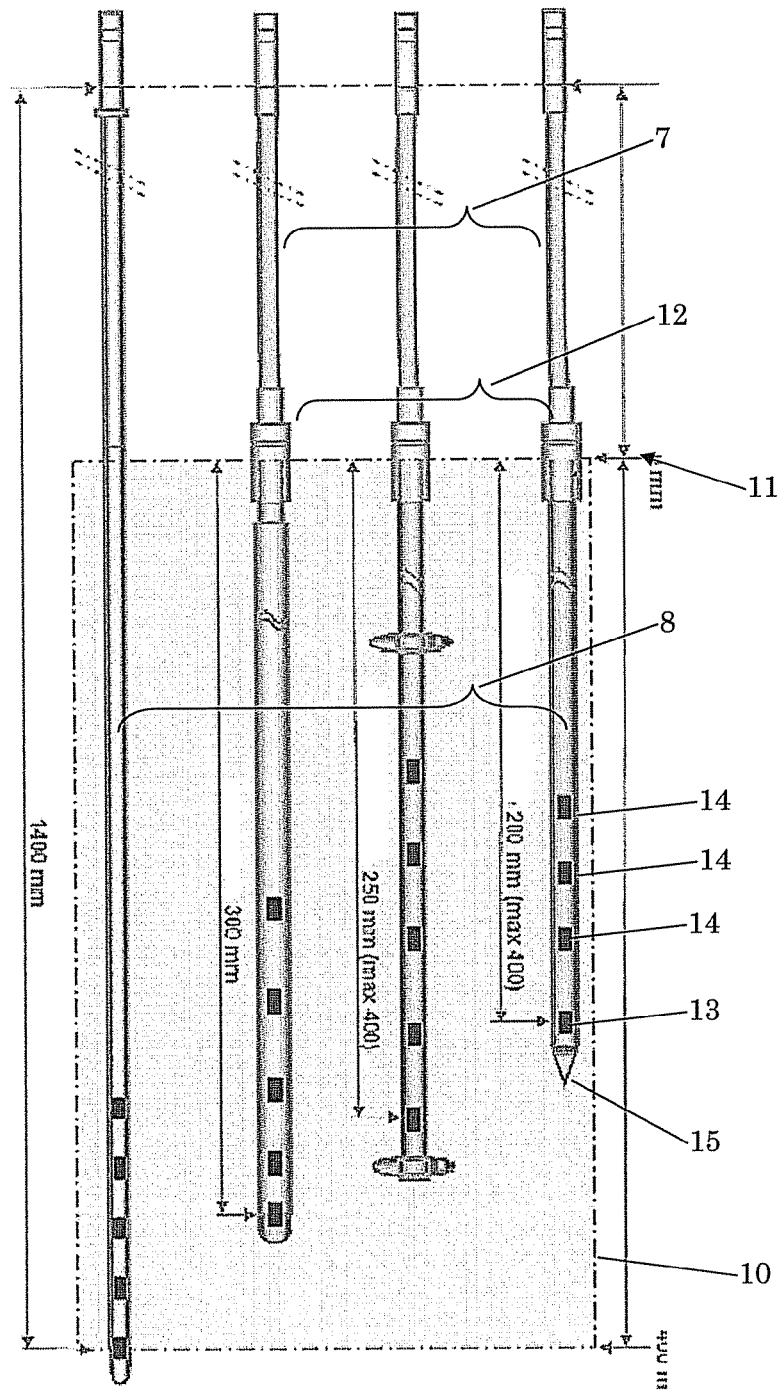
FIG. 2 shows a further illustration of the method used in the source guide system of FIG. 1.

FIG. 2 shows various metal and plastic tube shapes or catheters as used in brachytherapy in a straight or bent, rigid or flexible design.

As explained hereinabove, the catheters have an active range which falls within the range of the treatment window 10. In the cases shown under A-C in FIG. 2, active range is understood to mean a range formed by the proximal end 12 of the catheter, which forms a reference position 11, to a most distal dwell position 13 of a source. In the case shown under D, the active range is formed at a fixed distance from the proximal part 12 of the catheter to a most distal dwell position 13 of a source. This fixed distance is about 1000 mm in the exemplary embodiment, and may more in general be a fixed length of l×100 mm, l being a natural number. In the Figure, further, intermediate dwell positions 14 are schematically shown. The source guide apparatus 1 may be arranged to take up these dwell positions 14 in a stepwise manner and to dwell in respective dwell positions 13, 14 for predetermined times. Here, the step size may be programmable, for instance in steps of a multiple of 1 mm, and the dwell time may be settable, for instance a time programmable from about 0.1 sec to, for instance, about 999.99 sec. Importantly, while the duration of such dwell times can so vary from treatment to treatment, use to use of the invention, the individual dwell times provided in specific treatment episodes are precisely made by the invention.

In the exemplary embodiment shown under D (which is not intended to limit the invention), the catheter 8 is preferably directly connected to the source guide apparatus 1 (not shown). In the other cases A-C shown, conversely, the catheter 8 is preferably connected to the source guide apparatus 1 via a transit tube 7 (so-called remote afterloading apparatus). Here, the length of this transit tube 7 is preferably exactly 1000 mm or, more in general, a fixed length of l×100 mm, l being a natural number. In this manner, it is achieved that the treatment window 10 within which the irradiations are carried out can be set from a fixed reference position 11 with respect to the proximal end 12 of the catheter.

In above-mentioned cases A-D, the distal end 15 of the catheter 8 may even be outside the range of the treatment window 10, depending on the shape of the whole source and the shape of the catheter and tip, and therefore not contribute to above-mentioned active range of the catheter.

More specifically, in the following, the different catheters shown under A-D will be discussed.

The first catheter A indicates a needle which occurs both in metal and in various plastic forms. The metal needles often have a fixed length. Typical lengths may be about 50 mm, about 100 mm, about 150 mm, about 200 mm and about 250 mm. The plastic design is often about 200 mm or more and may be cut off as desired.

The second catheter B indicates a flexible catheter. These catheters can be cut off in various places after insertion into the tissue of the patient, but may also be provided with a fixed coupling so that the reference position "0" will be on the front side of the coupling instead of on the front side of the tube.

The third catheter C indicates a gynecologic applicator tube. It has a length of, e.g., 300 mm and is provided with a fixed coupling. The front side of this coupling is the reference position "0".

The fourth catheter D shows a long catheter which can inter alia be used for the bronchus, esophagus or bile duct. In this embodiment, the source guide system is arranged for guiding and locating a radiation source in a human body via a catheter which is directly connected to the apparatus via an adapter, without transit tube. Here, a treatment window is defined which expands from a reference position to positions situated within the body, while the reference position is situated at a predetermined distance with respect to the proximal end of the catheter, in this case a fixed length of about mm. The total length is thus fixed at, e.g., 1400 mm, the last 400 mm providing a treatment range which is within the treatment window. The choice of the four above tubes with their specifically chosen lengths makes the positioning of the source unambiguous and can remove much confusion.

Figure 3:
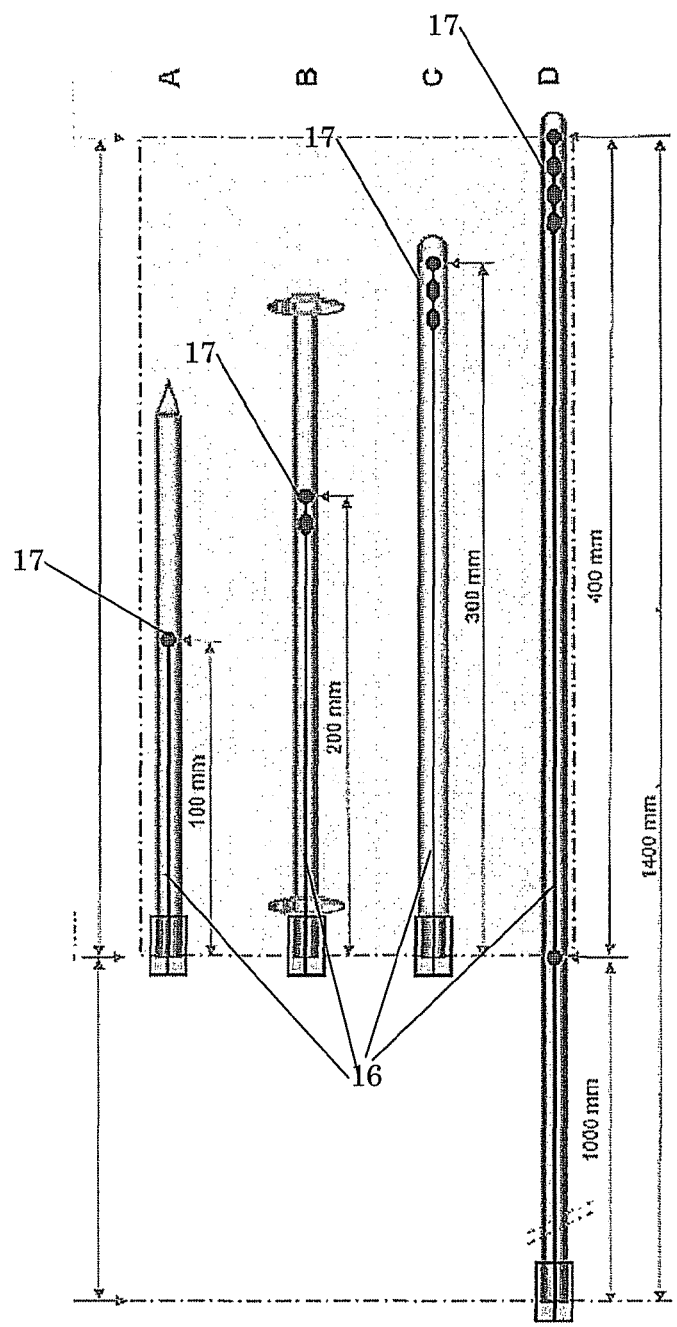
FIG. 3 shows an embodiment of the marker system according to another aspect of the invention.

FIG. 3 shows, according to another aspect of the invention, a set of markers 16 which can be used to be able to measure the catheters after placement in the patient. This measuring can be done by measuring the geometry of the tubes with respect to the area to be irradiated with the aid of X-ray or digital diagnostic techniques.

With the use of these markers, the concept of a fixed treatment window is the central point and, in the catheter, a single marking 17 is provided representing a fixed distance in the treatment window. This fixed distance is preferably expressed by a number of marker spots, while a position of m marker spots indicates an active range of m×100 mm with respect to the reference position in the treatment window.

The markings make reading quick and unambiguous and remove the confusion. In addition, the new design can be used in many different lengths of catheters and can simply be distinguished by using 1, 2, 3 or 4 markers. This is in contrast with the current practice, where often markers are used which have a marker clamped on a metal wire every, e.g., 10 mm. This results in a large number of markers on an X-ray or screen which are difficult to read with larger numbers which may cause errors in the irradiation calculation.

Figure 4:
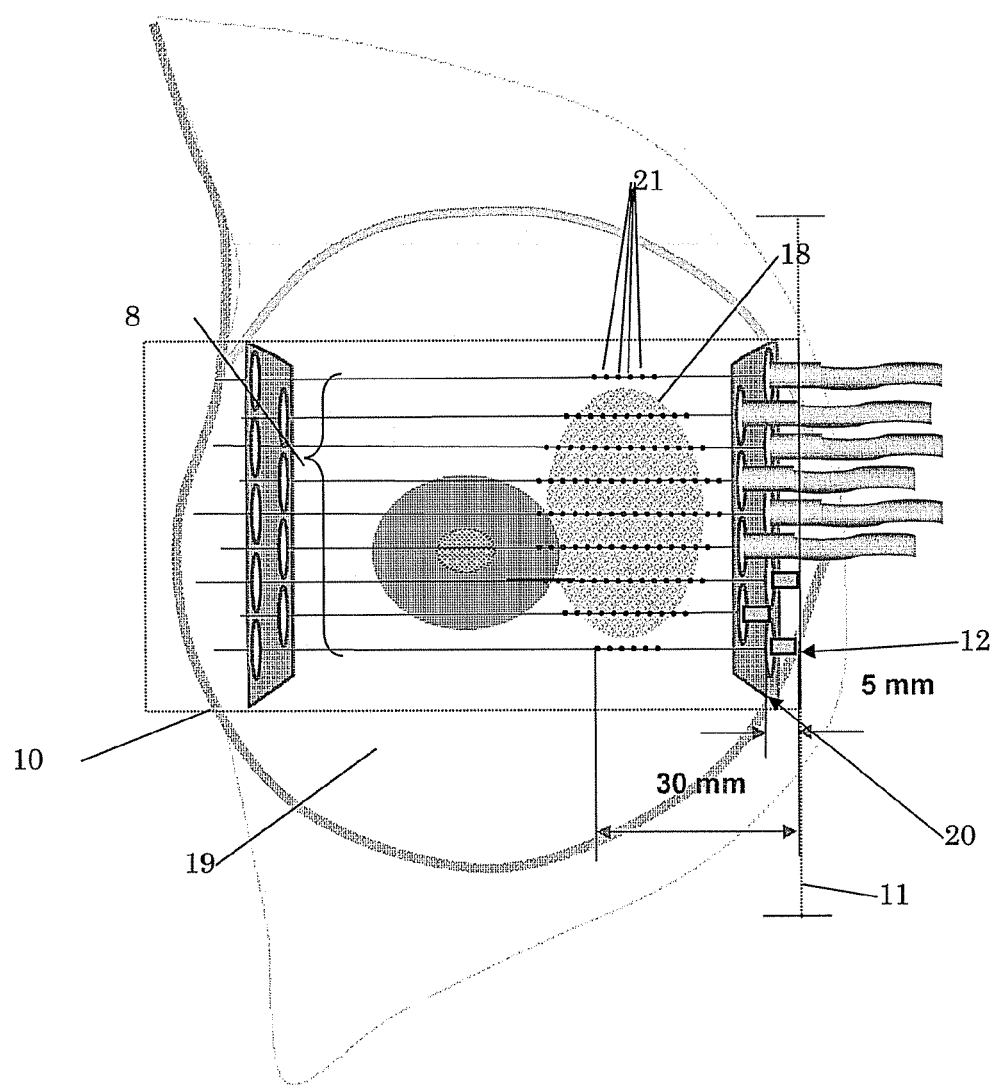
FIG. 4 shows an illustrative application of the invention.

FIG. 4 shows an illustrative application of the concept of the invention with the irradiation of a mammary carcinoma 18 in breast tissue 19. To this end, a plurality of catheters 8 are provided in the breast 19, and cut off near the entry 20 in the tissue 19. In the example of the Figure, the distance between the proximal end 12 and the entry is 5 mm. The proximal end 12 of the catheters 8 thus defines a fixed reference position 11, so that the treatment window 10 of the irradiation apparatus is expanded to positions situated within the breast 19. Within the treatment window 10, the source can be kept in respective positions 21, and while the reference position 11 is situated at a predetermined distance with respect to the proximal end 12 of the catheter 8.

Figure 5:
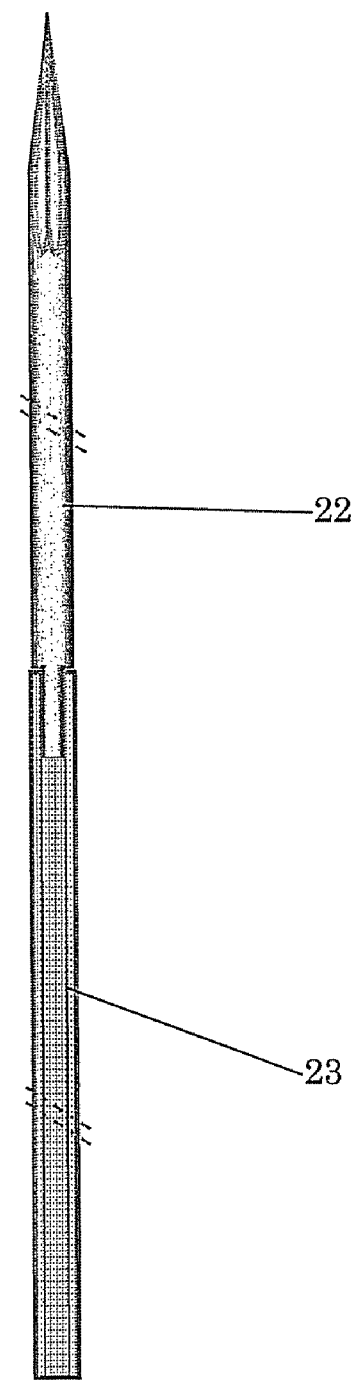
FIG. 5 shows a further illustration of a catheter for use of the invention.

FIG. 5 finally shows a catheter which can be used in an embodiment, to keep the proximal end of the catheter 8 at a predetermined distance with respect to the body, in particular such that this end preferably ends directly outside the body 3. This can be achieved by a catheter 8, comprising a stiff leading needle 22 with a flexible tube 23 coupled thereto, which can be shortened. Upon being guided through the tissue, the leading needle may possibly exit the body and be cut off.

Accordingly, the invention also provides a method for reducing medical errors associated with locating a radiation source in a human body comprising precisely locating, in time and space, a radiation source in a human body, which source is provided in a catheter and is connected to a source guide apparatus, and wherein the proximal end of the catheter is situated in a predetermined position with respect to the body, comprising:

defining a treatment window, which expands from a reference position to positions situated within the body, and wherein the reference position is situated at a predetermined distance with respect to the proximal end of the catheter;

locating the source relative to the treatment window; and maintaining the radiation source in the treatment window in a human body for a predetermined length of time. By "medical errors" it meant unintended exposures to the radiation source that result in clinically apparent morbidity or mortality, unrelated to the intended therapeutic goals. By "reducing medical errors" it is meant decreasing the incidence of such medical errors by at least about 5% per treatment course, preferably by at least about 10% per treatment course, more preferably by at least about 15% per treatment course, most preferably by at least about 20% per treatment course.

The invention is not limited to the embodiments shown in the drawing but may also comprise alternatives or variants thereof which fall within the scope of the following claims. Such variants may, for instance, comprise alternative coupling mechanisms, while the reference position "0" will always be on the front side of the entry of the coupling. Further, as discussed, the invention can employ only a single catheter or a plurality of catheters, including—for example, at least about 20 catheters, preferably at least about 15 catheters, more preferably at least about 10 catheters, most preferably at least about 2 catheters.

The invention claimed is:

1. A source guide apparatus for guiding and locating a radiation source in a human body, wherein a catheter is provided in a body and connected to the apparatus via a guide tube, comprising: a setting unit for setting source positions and source dwell times in a treatment window, which expands from a reference position to positions situated within the body, and wherein the reference position is situated on the proximal end of the catheter; and a control unit for guiding the source through the catheter to a predetermined position in the body, according to source positions indicated by the setting unit, measured relative to the treatment window.

2. A source guide apparatus according to claim 1, arranged for keeping the source in any one of a number of fixed, presettable positions in the treatment window.

3. A source guide apparatus according to claim 2, wherein the presettable positions have a mutual distance of about 1 mm or a multiple thereof.

4. A source guide apparatus according to claim 1, wherein the window has a fixed width that is n×100 mm, wherein n is a natural number.

5. A source guide apparatus according to claim 1, further including the catheter that can be shortened for having a proximal end at a predetermined distance with respect to the body.

6. A source guide apparatus according to claim 1, further comprising a single marking provided in the catheter which represents a predetermined active range of the catheter in the treatment window.

7. A source guide apparatus according to claim 6, wherein, for one fixed m, a marking is provided at a distance of m×100 mm with respect to the reference position, wherein m is a natural number, for representing an active range of m×100 mm.

8. A source guide apparatus according to claim 7, wherein the marking comprises m marker spots.

9. A source guide apparatus according to claim 5, further comprising a guide tube of a predetermined fixed length which is couplable with the source guide apparatus.

10. A source guide apparatus according to claim 9, wherein the guide tube has a fixed length of l×100 mm, wherein l is a natural number.

11. A source guide apparatus according to claim 10, wherein l is 10.

12. A method for locating a radiation source in a human body, which source is provided in a catheter and is connected to a source guide apparatus, and wherein the proximal end of a catheter is situated in a predetermined position with respect to the body, comprising: defining a treatment window, which expands from a reference position to positions situated within the body, and wherein the reference position is situated on the proximal end of the catheter; and locating the source relative to the treatment window.

* * * * *